United States Patent [19]

LeVeen et al.

[11] Patent Number: 5,156,164
[45] Date of Patent: Oct. 20, 1992

[54] IODINE CONTRACEPTIVE SPONGE

[76] Inventors: Harry H. LeVeen, 321 Confederate Cir., Charleston, S.C. 29407; Robert F. LeVeen, 312 Lombard St., Philadelphia, Pa. 19147

[21] Appl. No.: 650,985

[22] Filed: Feb. 4, 1991

Related U.S. Application Data

[60] Division of Ser. No. 318,178, Mar. 2, 1989, Pat. No. 5,000,749, which is a continuation-in-part of Ser. No. 257,062, Oct. 13, 1988, Pat. No. 4,968,439.

[51] Int. Cl.$^5$ .............................................. A61F 13/20
[52] U.S. Cl. .................................. 128/832; 128/833; 604/55; 604/890.1
[58] Field of Search ............... 128/833, 830, 831, 832; 604/11, 265, 55

[56] References Cited

U.S. PATENT DOCUMENTS

| | | | |
|---|---|---|---|
| 3,993,073 | 11/1973 | Zaffaroni | 128/833 |
| 4,292,965 | 10/1981 | Nash et al. | 128/833 |
| 4,309,997 | 1/1982 | Donald | 604/11 |
| 4,344,930 | 8/1982 | Macrae et al. | 424/28 |
| 4,381,380 | 4/1983 | Leveen et al. | 604/265 X |
| 4,393,871 | 7/1983 | Vorhauer et al. | 128/833 |
| 4,483,771 | 11/1984 | Koch | 210/490 |
| 4,551,148 | 11/1985 | Riley, Jr. et al. | 128/833 X |
| 4,553,972 | 11/1985 | Vickery | 128/833 X |
| 4,661,101 | 4/1987 | Sustmann | 604/360 |
| 4,731,391 | 3/1988 | Garvey | 521/137 |
| 4,784,989 | 11/1988 | Hook et al. | 514/21 |
| 4,957,119 | 9/1990 | de Nijs | 128/833 X |

FOREIGN PATENT DOCUMENTS

| | | |
|---|---|---|
| 2355895 | 5/1974 | Fed. Rep. of Germany ...... 210/501 |
| 2395746 | 1/1979 | France . |

OTHER PUBLICATIONS

Leveen et al.; "Chemical Acidification of Wounds: an Adjuvant to Healing and the Unfavorable Action of Alkalinity and Ammonia"; pp. 745–752; *Annals of Surgery;* vol. 178, No. 6; Dec. 1973.

Primary Examiner—Robert A. Hafer
Assistant Examiner—Kerry Owens
Attorney, Agent, or Firm—John S. Hale

[57] ABSTRACT

A bacteriocidal virocidal sponge containing iodine and a surfactant which can be used as a contraceptive and as therapy for vaginitis. It consists of a polyurethane open cell foam impregnated with a surfactant and iodine. A bactericidal tampon containing an iodophor does not induce toxic shock syndrome.

9 Claims, 2 Drawing Sheets

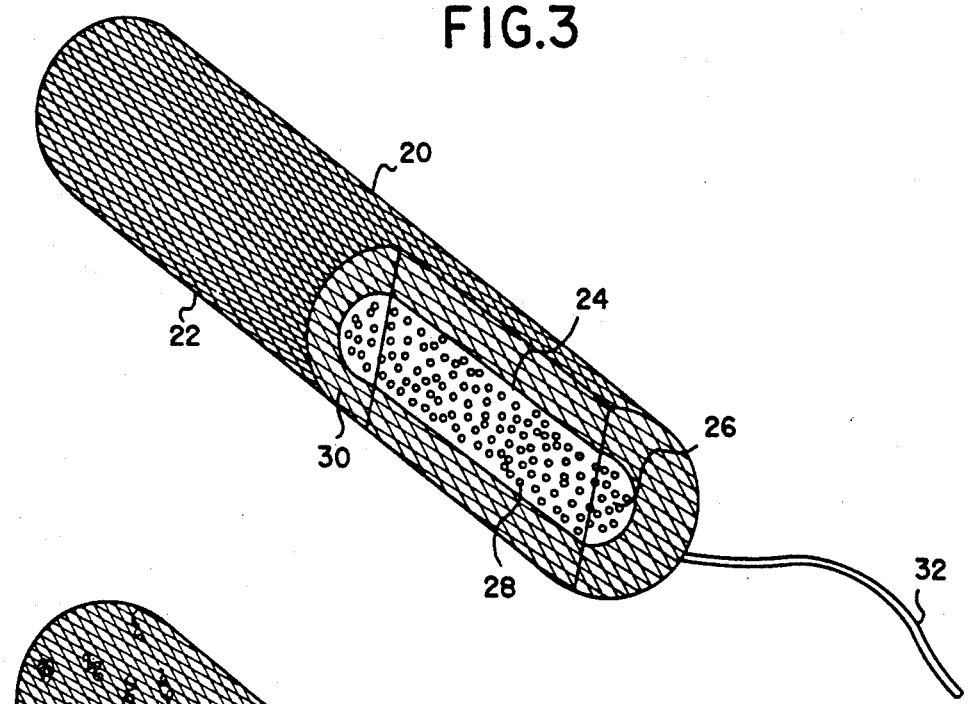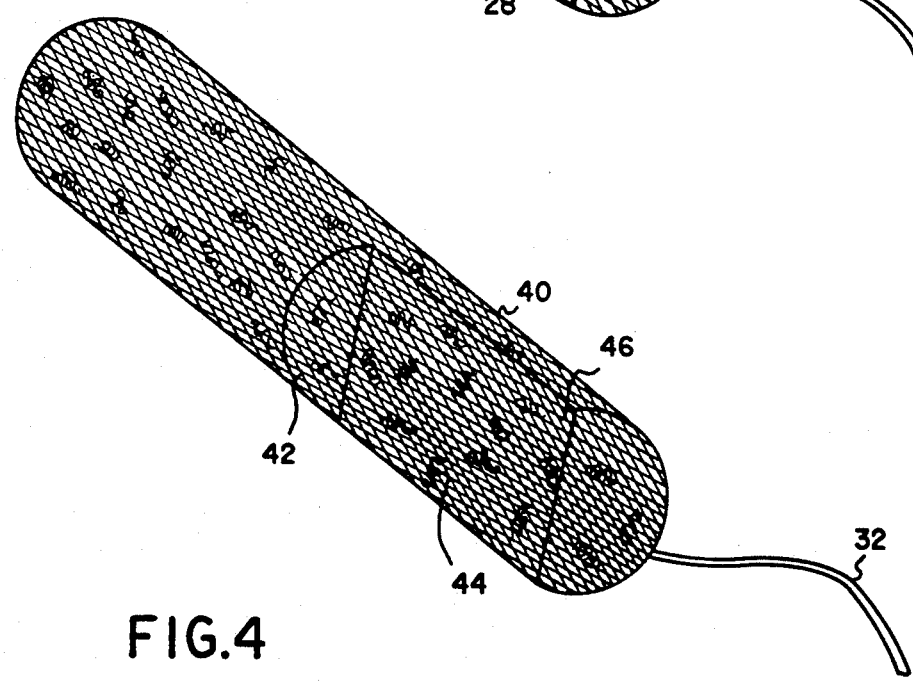

IODINE CONTRACEPTIVE SPONGE

RELATED APPLICATIONS

This is divisional of 318178 filed Mar. 2, 1989, now U.S. Pat. No. 5,000,749 which is a continuation-in-part application of U.S. patent application Ser. No. 257,062 filed Oct. 13, 1988, now U.S. Pat. No. 4,968,439.

BACKGROUND OF THE INVENTION

In recent years there has been a serious increase in sexually transmitted disease. Sexual freedom among consenting adults has been a partial cause of this increase. In addition, oral contraceptives and a change in the mores has created a situation which has increased the number of sexual contacts, thus favoring dissemination of sexually transmitted disease. Since these factors are unlikely to change, sexually transmitted disease has now become a major public health problem. Some diseases which were formerly unassociated with sexual transmission such as B virus hepatitis are now known to be sexually transmitted. Other new diseases such as acquired immune deficiency syndrome (AIDS) are viral diseases which are usually transmitted sexually. A need therefore exists for all conceivable types of control measures to reverse the increasing incidence of sexually transmitted disease.

The intravaginal contraceptive doughnut shaped sponge containing a spermicidal agent has become an accepted method of birth control in western society. Yet this sponge does little to halt the incidence of sexually transmitted disease which is steadily increasing. Such sponges are formed of an open cell polyurethane foam sponge impregnated with a spermicidal agent, nonoxynol-9, (U.S. Pat. No. 2,541,103). Nonoxynol is a polyethylene glycol nonylphenyl ether which is a mild surfactant. Like other non ionic surfactants it is a cytolytic agent which acts by disrupting the plasma membrane of animal cells. It is not as effective on the cell walls of bacteria which are unlike the lipid containing membranes of animal cells. Unfortunately, nonylphenoxypolyethoxyethanol is only bacteriostatic and not bacteriocidal when placed in a culture of staphlococcus aureus (TSS-S aureus). Toxic shock syndrome (TSS) is caused by the proliferation of staphlococcus aureus in absorbent tampons at the time of menstruation and in contraceptive sponges used in the absence of menstruation. Although nonoxynol does suppress colony counts of staphlococcus aureus during the first 6 hours of growth in a culture medium, the number of bacteria in the culture flask after 30 hours has been shown to be identical to that of control cultures. (Contraception 33:395 1986). Therefore, nonoxynol does not prevent the growth of staphlococci in contraceptive sponges. The absorption of the toxins from proliferating staphlococci can produce toxic shock syndrome. Thirteen cases have been reported in users of a contraceptive sponge impregnated with nonoxynol. (Int Fertil [Sweden] 30:81 1985). In all of these cases, TSS-S aureus was cultured. It has been estimated that the incidence of TSS would be 10 cases a year per 100,000 women using the sponge. The current mortality from TSS is 3% (J.A.M.A. 251:1016 1984). The death rate in contraceptive sponge users is less than that occurring with tampons where the incidence of TSS is also 10 per 100,000 menstrual users (NEJM 303:1429 1980). Even though nonoxynol is only bacteriostatic, a study of prostitutes in Bangkok, Thailand who used nonoxynol-9 intravaginal contraceptive sponges showed that these prostitutes had a lower incidence of venereal disease (chlamydial infection and gonorrhea) than those who did not use this contraceptive sponge. (J.A.M.A. 257:2308 1987). The incidence of monilia vaginitis was increased because nonoxinol is not fungicidal. The slight reduction in the incidence of venereal disease in frequently exposed prostitutes is not acceptable with regard to disease prevention and the decrease in incidence is eventually eliminated by frequency of exposure. If a contraceptive sponge could be made which was spermicidal, virocidal, bactericidal and fungicidal, it would completely protect against sexually transmitted disease. Such a sponge would not only protect the female from sexually transmitted disease, but would be equally protective for the male. This consideration has not been addressed by the medical literature. Bactericidal tampons would eliminate the possibility of toxic shock syndrome. Such developments would fulfill major public health needs and lead to a reduction in the rate of sexually transmitted disease.

SUMMARY OF THE INVENTION

The present invention describes a bactericidal, virocidal and protozocical contraceptive sponge which unlike a sponge which relies totally on a weak bacteriostatic compound will prevent sexually transmitted disease caused by viruses and bacteria and is useful in treating vaginal infections (vaginitis) caused by trichomonas, gonococcus, monilia and chlamydia. It also describes a vaginal absorbent tampon which cannot induce toxic shock syndrome. Furthermore, such a contraceptive sponge may prevent the carcinoma of the cervix which is now known to be a manifestation of the sexually transmitted papilloma virus, In addition, transmission of the highly prevalent genital herpes which is known to predispose to malignancy may be prevented.

The present invention discloses a sponge which liberates small amounts of iodine from a polyurethane iodine complex sufficient to make it bactericidal, spermicidal, virocidal and protozolcidal without being irritative. It thus can be used as a contraceptive and w±ll prevent sexually transmitted disease and Toxic Shock Syndrome. It is also suitable as a therapy for all types of infectious vaginitis. The iodine liberating polyurethane sponge can be incorporated into vaginal tampons as a protective against toxic shock syndrome which is a serious threat to women using a tampon as an absorbent during menses.

BRIEF DESCRIPTION OF THE DRAWINGS

FIG. 3 is a tampon using the sponge invention partially cut away to show a section of the interior; and FIG. 4 is another embodiment of the tampon invention partially cut away to show a section of the interior.

DETAILED DESCRIPTION OF THE INVENTION

Figure 1:
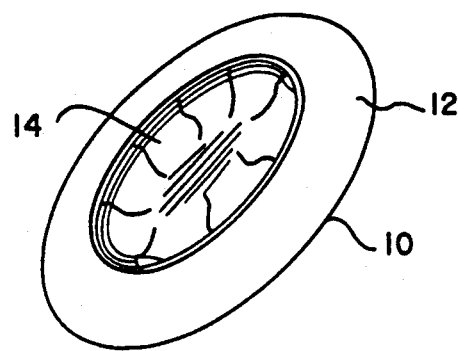
FIG. 1 is a perspective view of the contraceptive sponge invention.

The best mode and preferred embodiment of the invention is shown in FIG. 1. Iodine in concentration of 2+ parts per million is a strong disinfectant. Such concentrations of iodine are known to be germicidal, algaecidal, sporocidal, amoebacidal, mycocidal and viricidal.

The reduction of venereal disease by those who use a simple contraceptive sponge indicates that if the intravaginal contraceptive sponge were also spermicidal, bacteriocidal and virocidal, it would be a very efficient contraceptive and in addition it would protect against sexually transmitted disease and Toxic Shock Syndrome.

$I_2$ bonds to PVP between the carbonyl group and the nitrogen. $I_2$ complexes with polyurethane and releases the $I_2$ in a manner similar to PVP (U.S. Pat. No. 4,381,380). Solid polyurethane-$I_2$ sponge has a large surface area whether made by foaming thermoplastic polyurethane with a blowing agent or making the sponge with a blowing agent as a thermoset. The latter method is usually employed in making polyurethane foam and because of its large surface area can bind considerable quantities of iodine. Iodine has been found to possess superior germicidal properties. Polyurethane sponge by virtue of the great magnitude of surface area can bind large quantities of free iodine and is thus capable of liberating it continuously for many hours or days thus adding considerably to its therapeutic value.

Figure 2:
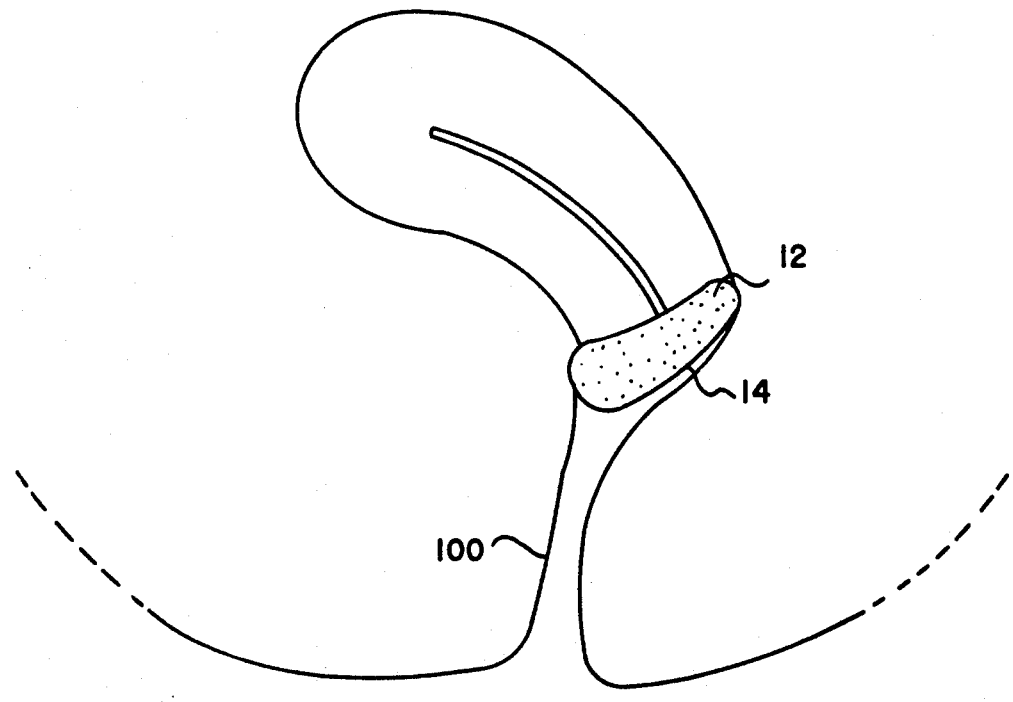
FIG. 2 is a partial cross section view of the sponge invention of FIG. 1 inserted into a cervical canal.

In the present invention a polyurethane contraceptive sponge 10 shaped like a shallow hat with a rim 12 and hollowed out concave central portion 14 is shown in FIG. 1. The sponge 10 forms a suitable barrier to the entrance of sperm into the cervical canal. Such a sponge is inserted into the vagina 100 in a folded position with the hollowed out concave portion 14 folded in and the edges on rim 12 pointing upward. After insertion the hollow area accommodates the cervix of the uterus as is shown in FIG. 2.

Iodine is complexed to polyurethane sponge 10 by the addition of free iodine in an aqueous solution of potassium iodide. Lugol's solution which is 5% $I_2$ dissolved in 10% sodium iodide solution can be used to complex the iodine with polyurethane. The sponge can be immersed in the Lugol's solution or the solution can be added drop wise to the sponge. The sponge is then washed with 0.2% sodium iodide solution to remove excess iodine and subsequently washed thoroughly with deionized water. Alternative methods are available to complex the sponge with iodine. The iodine can be dissolved in alcohol containing nonoxynol and allowed to dry depositing 20 to 40 mg of iodine for each gram of nonoxynol deposited. Alternatively, the iodine can be added to the nonoxynol prior to its addition to the sponge so that each sponge contains about 1 gram nonoxynol and 20 to 40 mg. iodine. Iodine is dissolved by surfactants such as nonoxynol which are themselves iodophors. Since iodine is more effective in acid solution, 5-20 milligrams of polyacrylic acid (Carbopol made by Goodrich) is added to keep the vaginal secretions acid.

The sponges can be obtained from any number of manufacturers for example the Scott Co. which specialize in open cell foams for air filters. The sponges should be flexible and therefore polyether polyurethane rather than polyester. Polyether polyurethanes are more suitable although both function satisfactorily as iodine binders and an admixture of both may be necessary to arrive at a satisfactory durometer. The sponge should have very small open cells and as high a density as is compatible with maximum porosity. This exposes a maximum number of urethane linkages on the surface of the polyurethane where the complexing with the iodine takes place.

Aqueous saline solution with 2-4 ppm of $I_2$ is not inflammatory when instilled into the human eye and can be used to irrigate human tissue to prevent infection or to treat infected peritonitis (Stephen RL et al Dialysis & Transplantation page 662 June 1979). Aqueous Iodine solution U.S.P. which contains 2% iodine in 2.4% sodium iodide is mentioned in A.M.A. Drug Evaluations 5th Ed. 1983 page 1385 as "preferred for superficial lacerations to prevent micobial infections, since it is effective and nonirritating." $I_2$ is an excellent broad spectrum non selective biocidal agent to which organisms do not develop resistance. $I_2$ has been locally used to treat bacterial and mycotic infections including bacterial skin infections, sore throats and mycotic infections of the toes, hands, ears, or perineal region. (J. Internat. Col. Surg. 25:727 1956) with clearing in 36 hours. Iodine has been successfully used to control infection on burns and traumatic skin loss (Brit. J. Plastic Surg 28:146 1965). Its use to sterilize the skin prior to surgical operations is well known although the use of the tincture has largely been replaced with iodophors, such as polyvinylpyrrolidone-iodine complex. Iodophors have been found to be effective in treating resistant vaginitis (Current Ther. Res. 5:256 1963). Iodine is effective against monilia (Plastic & Reconstruct. Surg. 29:648 1962), and trichomonas (J. Newark Beth Israel Hosp. 6:129 1955) as well as bacterial infections.

In most studies, the iodine was applied as a polyvinylpyrrolidone-iodine complex from which free iodine is liberated (U.S. Pat. No. 2,739,922). Tampons impregnated with PVP-iodine were used in most studies on vaginitis. PVP iodine has the disadvantage of being a brown liquid. It would be better if the iodophor were a solid and not a liquid.

EXAMPLE

Iodine sponges are effective in the treatment of senile vaginitis. In this disease, the absence of estrogens causes the failure of glycogen to appear in the vaginal mucosa. The vaginal secretions are kept acid by Doderlin bacteria normally present in the vagina which convert the glycogen to lactic acid. This neutralizes and makes non toxic the ammonia which would otherwise form in the vagina and irritate and inflame the vaginal mucosa. The iodine kills the urease producing bacteria and thus interrupts the production of ammonia. Polyacrylic acid restores the acidity of the vaginal secretions. The polyurethane-iodine sponge is curative for senile vaginitis. Similarly, the polyurethane-iodine sponge has been curative for vaginitis caused by trichomonas, monilia, herpes, gonorrhea and other infective types of vaginitis. In such cases a new sponge is introduced once or twice a day for 5 days. Cultures or smears have confirmed the disappearance of monilia and trichomonas.

Another use of the iodine sponge is in absorbent tampons which are used by many females at the time of menses. All of these tampons are barriers which impede the discharge of shed blood and tissue and prolong its retention in the vagina. When those protein soaked tampons become contaminated with staphlococcus aureus, bacterial growth in the tampon can result in a high concentration of toxic bacterial products within the tampon. Absorption of these staplococcal toxins causes toxic shock syndrome characterized by fever, hypotension, nausea, lethargy, diffuse rash, desquamation, and a vaginal discharge. Vaginal cultures are positive for staphlococcus aureus. A mortality rate of 3% attests to the seriousness of the disease. The occurrence of toxic shock syndrome could be eliminated by making the tampons bactericidal. This can be done by incorporating polyurethane iodine sponge as a central core of the tampon or as small pieces of shredded iodine polyurethane-iodine complex so as to store at least 40 mg of releasable iodine in the tampon.

FIG. 3 shows an absorbent tampon 20 with a gauze covering 22. The core member 24 of the tampon 20 is a polyurethane sponge 26 which has been complexed with at least 20 mg of releasable iodine and contains air bubble 28. Surrounding the core member 24 are absorbent cellulose fibers 30 which are covered by a wrapping of cotton gauze 22. A string 32 is attached to the gauze to permit withdrawal of the tampon.

An alternate tampon embodiment is shown in FIG. 4. The tampon 40 has an absorbent cellulose body 42 containing bits of polyurethane foam 44 which has been shredded and treated with iodine in the amount previously stated. The foam bits 44 are interplaced in absorbent cellulose 46. The tampon is wrapped with gauze (not shown) identical to the tampon of FIG. 3 and is provided with a similar string.

In the foregoing description, the invention has been described with reference to a particular preferred embodiment, although it is to be understood that specific details shown are merely illustrative, and the invention may be carried out in other ways without departing from the true spirit and scope of the following claims:

What is claimed:

1. A bactericidal spermicidal sponge member for insertion into the vagina in the form of an open cell foam impregnated with an iodine polyurethane complex and containing a nonionic spermicidal surfactant, said foam continuously liberating free iodine into the human body in a concentration ranging from 2 to 5 parts per million.

2. A spermicidal sponge member as claimed in claim 1 wherein said sponge comprises a hat shaped configuration comprising a body with a circular rim with a concave interior portion.

3. A spermicidal sponge member as claimed in claim 1 wherein said surfactant is nonoxynol.

4. A sponge member as claimed in claim 1 wherein said sponge contains nonoxynol and iodine with 20 to 40 mg iodine deposited on the sponge for each gram of nonoxynol deposited.

5. A sponge member as claimed in claim 1 wherein said open cell foam is treated with a solution of elemental iodine dissolved in a non ionic surfactant.

6. A sponge member as claimed in claim 5 wherein said surfactant is an acid solution ranging from 5 to 20 milligrams is added to the sponge to keep the vaginal secretions acid.

7. A sponge member as claimed in claim 6 wherein said acid solution is polyacrylic acid and the amount added ranges from 5 to 20 milligrams.

8. A contraceptive device for women comprising a sponge member formed of a polyether open cell foam complexed with iodine and a surfactant means in an aqueous medium to enhance the spermicidal effect of the iodine, said sponge member additionally containing polyacrylic acid to restore vaginal acidity and being bactericidal, spermicidal and viricidal and continuously liberating free iodine into the human body after insertion.

9. A contraceptive device for women comprising a circular shaped sponge member, said sponge member being formed of a polyether open cell foam complexed with iodine and a nonionic spermicidal surfactant, said sponge member additionally containing polyacrylic acid and being bactericidal, viricidal and spermicidal and continuously liberating iodine into the human body after insertion.

* * * * *